US00PP29503P3

(12) United States Plant Patent
Guzman

(10) Patent No.: US PP29,503 P3
(45) Date of Patent: Jul. 17, 2018

(54) ***CHAMAECYPARIS* PLANT NAMED 'MONYUR'**

(50) Latin Name: *Chamaecyparis obtusa*
Varietal Denomination: MonYur

(71) Applicant: Pedro Quevedo Guzman, Salem, OR (US)

(72) Inventor: Pedro Quevedo Guzman, Salem, OR (US)

(73) Assignee: Monrovia Nursery Co., Azusa, CA (US)

( * ) Notice: Subject to any disclaimer, the term of this patent is extended or adjusted under 35 U.S.C. 154(b) by 83 days.

(21) Appl. No.: 15/330,520

(22) Filed: Sep. 30, 2016

(65) Prior Publication Data

US 2018/0098473 P1 Apr. 5, 2018

(51) Int. Cl.
*A01H 7/00* (2006.01)

(52) U.S. Cl.
USPC ..... Plt./213
CPC ..... *A01H 7/00* (2013.01)

(58) Field of Classification Search
USPC ..... Plt./213
CPC ..... A01H 7/00; A01H 5/00
See application file for complete search history.

*Primary Examiner* — Kent L Bell
(74) *Attorney, Agent, or Firm* — Cassandra Bright

(57) ABSTRACT

A new and distinct *Chamaecyparis* cultivar named 'MonYur' is disclosed, characterized by distinctive compact plant form, slow growth and dense branching. Plants' distinctive growth habit result in reduced need for pruning. The new cultivar is a *Chamaecyparis*, suitable for ornamental garden purposes.

1 Drawing Sheet

Latin name of the genus and species: *Chamaecyparis obtusa.*

Variety denomination: 'MonYur'.

BACKGROUND OF THE INVENTION

The new cultivar is a product of chance discovery by the inventor, Pedro Guzman. This new variety, hereinafter referred to as 'MonYur', was selected as a naturally occurring, whole plant mutation from an unnamed, unpatented plant of *Chamaecyparis obtusa*. The novel variety was discovered in a commercial nursery in Dayton, Oreg. during August of 2010.

After identifying the new variety as a potentially interesting selection, first propagation of 'MonYur' occurred by hardwood cuttings at the same commercial nursery during February of 2011. The inventor continued controlled testing and propagation, assessing stability of the unique characteristics of this variety. Three generations have been asexually reproduced and have shown that the unique features of this cultivar are stable and reproduced true to type.

SUMMARY OF THE INVENTION

The cultivar 'MonYur' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'MonYur' These characteristics in combination distinguish 'MonYur' as a new and distinct *Chamaecyparis* cultivar:

1. Compact growth habit.
2. Improved landscape performance due to lower pruning requirement.
3. Dense branching.

COMPARISON TO PARENT VARIETY

'MonYur' is similar in most horticultural characteristics to the parent variety. Plants of the new cultivar 'MonYur' however, are distinctively more compact, with lower pruning requirements.

COMMERCIAL COMPARISON

In addition to the seed parent, 'MonYur' can be compared to the commercial variety an unnamed plant of *Chamaecyparis obtusa filicoides*, unpatented. The varieties are similar in most horticultural characteristics, however, plants of 'MonYur' are more compact, and require less pruning. Ultimate height of the new variety is 6 to 8 feet, mature height of the comparator is 8 to 10 feet. Branches of the new variety are more tightly arranged.

'MonYur' can be compared to the commercial variety an unnamed plant of *Chamaecyparis obtusa gracilis*, unpatented. The varieties are similar in most horticultural characteristics, however, plants of 'MonYur' have a tighter, more compact plant form, requiring less pruning. Mature height of 'MonYur' is approximately 6 to 8 feet, mature height of this comparator is approximately 10 to 12 feet.

'MonYur' can be compared to the commercial variety an unnamed plant of *Chamaecyparis obtusa compacta*, unpatented. The varieties are similar in most horticultural characteristics, however, plants of 'MonYur' produce more branches, in a denser pattern, forming a tighter, more compact plant form. Plants of the new variety grow more slowly, requiring less pruning. Mature height of 'MonYur' is approximately 6 to 8 feet, mature height of this comparator is approximately 10 to 12 feet.

BRIEF DESCRIPTION OF THE PHOTOGRAPH

The accompanying photograph in FIG. 1 illustrates in full color a typical plant of 'MonYur' grown outdoors in Dayton, Oreg., next to the parent variety an unnamed plant of *Chamaecyparis obtusa*. The new variety, 'MonYur' is the smaller plant on the right side of the drawing. Plants of both the parent variety and new variety are approximately 72 months old from a rooted cutting, grown under identical conditions. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'MonYur' plants grown outdoors in Dayton, Oreg. Plants are approximately 3 years old, in a 7 gallon nursery container. Measurements and numerical values represent averages of typical plant types.

Botanical classification: *Chamaecyparis obtusa* 'MonYur'.

PROPAGATION

Time to rooting: 120 to 150 days at approximately 40-50° F.

Root description: Fibrous, very well branched. Colored near RHS Brown N199B.

PLANT

Growth habit: Upright, semi-pyramidal evergreen shrub.

Height: Approximately 100 cm. after 3 years.

Plant spread: Approximately 70 cm. after 3 years.

Typical growth rate: Slow.

Pinching required: No.

Branching characteristics: 1 to 3 main stems with approximately 20 to 40 lateral branches. Lateral stems are held at an angle of approximately 45 to 90 degree from the main stem. Main lateral branches have between 10 and 20 secondary branches each.

Length of lateral branches: Average range 20 to 50 cm.

Diameter of lateral branches: Average range 0.5 to 1.0 cm.

Lateral branch shape in cross section: Generally round.

Lateral branch strength: Very strong.

Lateral branch color: Mixture near Grey-Brown 199A, 199B and Greyed-Orange 177C.

Lateral branch texture: Rough and scaly.

Internode length: Average range between 0.5 and 1.0 cm.

FOLIAGE

General description: Tightly held, scales on planar branchlets.

Leaf:

- *Arrangement*.—Opposite.
- *Type*.—Flattened, nearly needlelike.
- *Shape of blade*.—Linear.
- *Average length*.—Approximately 2 mm.
- *Average width*.—Approximately 1.5 mm.
- *Apex*.—Acute.
- *Base*.—Obtuse.
- *Attachment*.—Sessile.
- *Margin*.—Entire.
- *Texture of top surface*.—Glabrous.
- *Texture of bottom surface*.—Glabrous.
- *Leaf internode length*.—Less than 1 mm.
- *Color*.—Young foliage upper side: Between Green 143B and 137C. Young foliage under side: Between Green 143B and 137C. Mature foliage upper side: Near Green 137C. Mature foliage under side: Near Green 137C.
- *Venation*.—Linear, indistinguishable from leaf blade.
- *Durability of foliage to stresses*.—Flexible and resistant to breakage.
- *Fragrance*.—Very mild cedar scent.

Branchlet:

- *Arrangement*.—Opposite on branches, sub-branchlets opposite and alternate occurring.
- *Branchlet internode*.—3 to 5 mm.
- *Average length*.—Approximately 3.2 to 6.0 cm.
- *Average width*.—Approximately 1.8 to 2.5 cm.

FLOWER

Flowering not observed.

OTHER CHARACTERISTICS

Disease and pest resistance: Neither resistance nor susceptibility observed.

Drought tolerance: No tolerance for drought.

Temperature tolerance: USDA Zones 4 through 8.

What is claimed is:

1. A new and distinct cultivar of *Chamaecyparis* plant named 'MonYur' as herein illustrated and described.

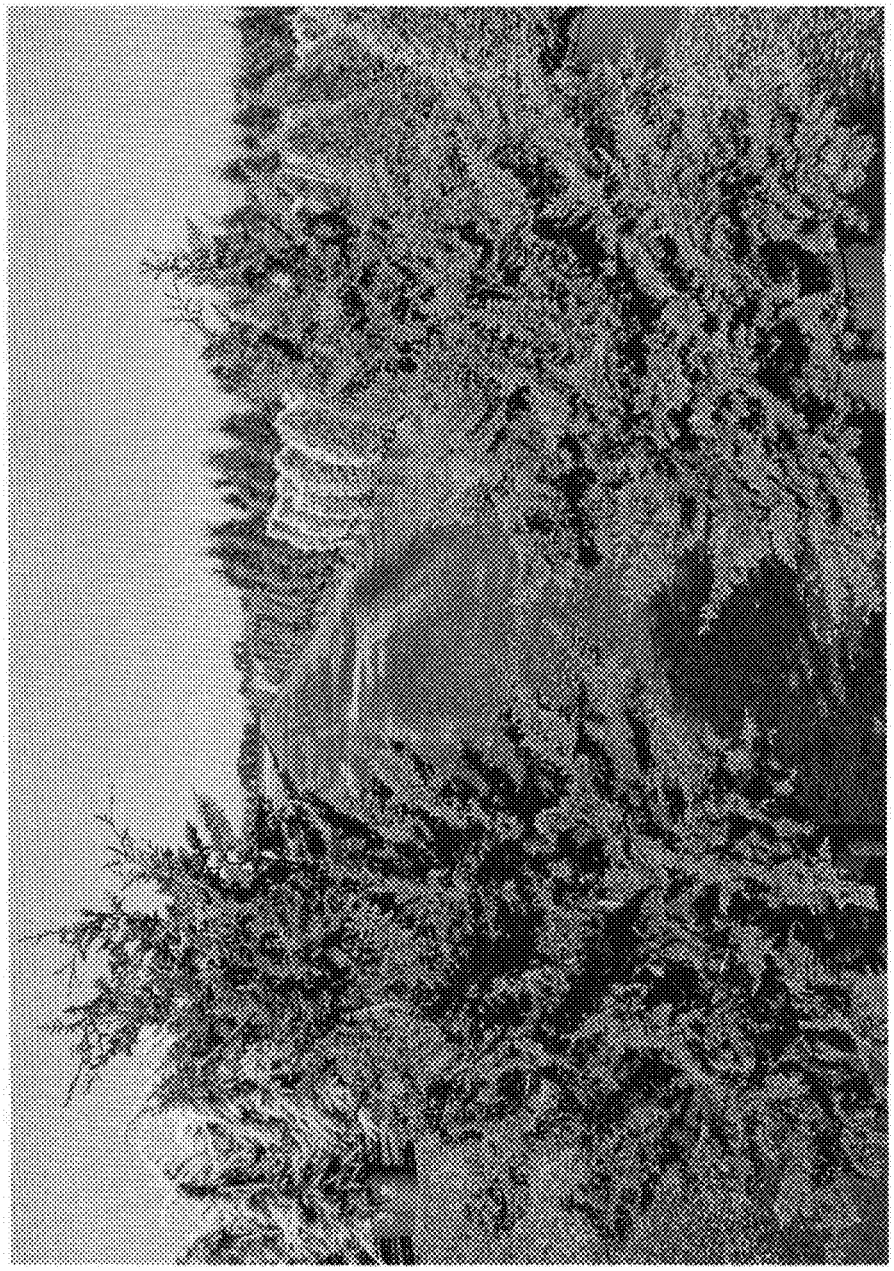

* * * * *